(12) United States Patent
DauSchmidt

(10) Patent No.: US 11,826,279 B2
(45) Date of Patent: Nov. 28, 2023

(54) EYELID TREATMENT DEVICE AND ASSOCIATED METHODS

(71) Applicant: Ken DauSchmidt, Hugo, MN (US)

(72) Inventor: Ken DauSchmidt, Hugo, MN (US)

(73) Assignee: Ken Dauschmidt, Hugo, MN (US)

(*) Notice: Subject to any disclaimer, the term of this patent is extended or adjusted under 35 U.S.C. 154(b) by 1285 days.

(21) Appl. No.: 16/083,229

(22) PCT Filed: Mar. 7, 2017

(86) PCT No.: PCT/US2017/021164
§ 371 (c)(1),
(2) Date: Sep. 7, 2018

(87) PCT Pub. No.: WO2017/156002
PCT Pub. Date: Sep. 14, 2017

(65) Prior Publication Data
US 2019/0083301 A1    Mar. 21, 2019

Related U.S. Application Data

(60) Provisional application No. 62/305,078, filed on Mar. 8, 2016.

(51) Int. Cl.
*A61F 7/03* (2006.01)
*A61F 7/10* (2006.01)
(Continued)

(52) U.S. Cl.
CPC ............... *A61F 7/034* (2013.01); *A61F 7/02* (2013.01); *A61F 7/106* (2013.01); *A61F 9/00* (2013.01);
(Continued)

(58) Field of Classification Search
CPC .... A61F 7/034; A61F 7/00; A61F 7/02; A61F 7/106; A61F 9/007; A61F 9/02; A61F 9/04
See application file for complete search history.

(56) References Cited

U.S. PATENT DOCUMENTS

| 5,368,582 A | 11/1994 | Bertera |
| 5,645,749 A * | 7/1997 | Wang ........................ A61F 7/03 |
| | | 219/745 |

(Continued)

FOREIGN PATENT DOCUMENTS

| WO | WO-2013073840 A1 | 5/2013 |
| WO | WO-2017156002 A1 | 9/2017 |

OTHER PUBLICATIONS

"International Application Serial No. PCT/US2017/021164, International Search Report dated May 19, 217", 2 pgs.

(Continued)

*Primary Examiner* — Tigist S Demie
(74) *Attorney, Agent, or Firm* — SCHWEGMAN LUNDBERG & WOESSNER, P.A.

(57) ABSTRACT

Implementations described herein include a device comprising a frame and an energy source operably coupled to the frame that applies energy to eyelids and allows for normal blinking of the eye. The frame is securably positionable on a face of a user. The frame includes an engagement portion operably coupled to a support portion. The engagement portion is positionable over an eye of a user. The engagement portion extends between a medial side and a lateral side thereof. The support portion is securable to the face of the user peripheral to an eye area thereof. The eye area includes both the upper eyelid and the lower eyelid of the eye. The engagement portion can be a first engagement portion and the frame can further include a second engagement portion spaced apart from the first engagement portion.

(Continued)

The first engagement portion and the second engagement portion can be coupled via a support portion extending therebetween.

13 Claims, 4 Drawing Sheets

(51) Int. Cl.
*A61F 9/02* (2006.01)
*A61F 9/007* (2006.01)
*A61F 9/04* (2006.01)
*A61F 7/02* (2006.01)
*A61F 9/00* (2006.01)
*A61F 7/00* (2006.01)
*A61M 35/00* (2006.01)

(52) U.S. Cl.
CPC ............... *A61F 9/007* (2013.01); *A61F 9/02* (2013.01); *A61F 9/04* (2013.01); *A61F 2007/0004* (2013.01); *A61F 2007/0226* (2013.01); *A61F 2007/0292* (2013.01); *A61M 35/10* (2019.05)

(56) References Cited

U.S. PATENT DOCUMENTS

| | | |
|---|---|---|
| 2006/0157064 A1 | 7/2006 | Davison et al. |
| 2011/0022010 A1* | 1/2011 | Grenon ............... A61H 7/00 604/294 |
| 2012/0003296 A1 | 1/2012 | Shantha et al. |
| 2015/0209174 A1* | 7/2015 | Abreu ................. A61F 7/02 607/104 |
| 2015/0283402 A1 | 10/2015 | Grenon et al. |

OTHER PUBLICATIONS

"International Application Serial No. PCT/US2017/021164, Written Opinion dated May 19, 2017", 5 pgs.
"International Application Serial No. PCT/US2017/021164, International Preliminary Report on Patentability dated Sep. 20, 2018", 7 pgs.

* cited by examiner

EYELID TREATMENT DEVICE AND ASSOCIATED METHODS

PRIORITY CLAIM

This patent application is a U.S. National Stage Application under 35 U.S.C. 371 from International Application No. PCT/US2017/021164, filed Mar. 7, 2017, which claims the benefit of the priority to U.S. Provisional Application Ser. No. 62/305,078, filed Mar. 8, 2016, which is incorporated by reference herein in its entirety.

FIELD

The present disclosure relates to an eyelid treatment device for applying energy to an eyelid and associated methods.

BACKGROUND

Meibomian Gland Disease (MGD) is the leading cause of dry eye. MGD occurs when glands in the eyelid, the meibomian glands, do not release sufficient amounts of the oils needed for a healthy tear film, leading to premature evaporation of the watery layer of the tear film. Patients with MGD can suffer from symptoms such as redness, tearing, burning or gritty sensations, blurry vision, and the like. MGD is a progressive disease but patients can benefit from therapies that encourage or promote production and/or release of the oils in the meibomian glands.

SUMMARY

The present inventors have recognized, among other things, that a problem to be solved can include applying energy to eyelids to treat the eyes while not inhibiting normal blinking of the eyes. The present subject matter can help provide a solution to this problem, such as by providing a device comprising a frame and an energy source operably coupled to the frame that can apply energy to eyelids and can allow for normal blinking of the eye. The frame can be securably positionable on a face of a user. The frame can comprise an engagement portion operably coupled to a support portion. The engagement portion can be positionable over an eye of a user. The engagement portion can extend between a medial side and a lateral side thereof. The support portion can be securable to the face of the user peripheral to an eye area thereof. The eye area can comprise both the upper eyelid and the lower eyelid of the eye. The engagement portion can comprise a first engagement portion and the frame can further comprise a second engagement portion spaced apart from the first engagement portion. The first engagement portion and the second engagement portion can be coupled via a support portion extending therebetween.

The present subject matter also provides for a method that can comprise (i) securably positioning a frame of a device to a face of a user, the device comprising: a frame that can be securably positionable on a face of a user, the frame comprising an engagement portion that can be operably coupled to a support portion, wherein the engagement portion can be positionable over an eye of a user, wherein the engagement portion can extend between a medial side and a lateral side, wherein at least a portion of the engagement portion can be contoured to match the shape of an upper eyelid or a lower eyelid of the eye of the user, wherein the support portion can be securable to the face of the user peripheral to an eye area thereof; and an energy source operably coupled to the frame; wherein the frame and the energy source cooperate to apply energy to the upper eyelid or the lower eyelid of the eye of the user without obstructing use of or normal blinking of the eye; and (ii) activating the energy source to apply energy to the upper eyelid or the lower eyelid of the eye of the user for a selected time and at a selected temperature.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, byway of example, but not by way of limitation, various embodiments discussed in the present document.

DETAILED DESCRIPTION

The present subject matter relates to devices comprising a frame and an energy source operably coupled to the frame that can apply energy to eyelids and can allow for normal blinking of the eye. The application of energy to the eyelids and target areas can provide a therapeutic benefit while not inhibiting blinking. In some examples, the energy source can be suspended over the eyelid(s) and, in other examples, the energy source can contact the eyelid(s). In some cases, it is contemplated that a user can engage in normal activities during use of the devices. Such devices and related methods can promote patient compliance and can result in enhanced therapeutic benefits.

Figure 1A:
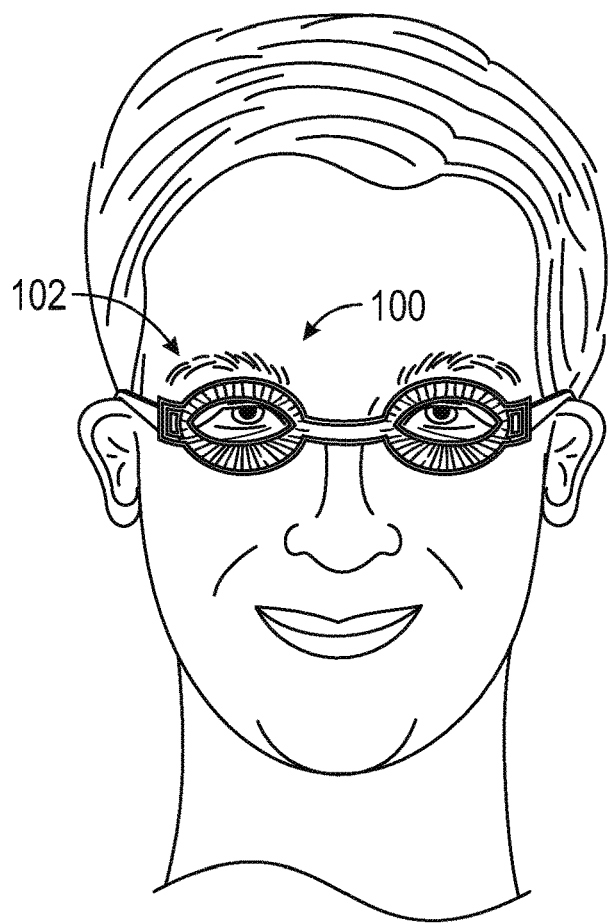
FIG. 1A is a perspective view of one example of a device according to the present disclosure worn by a user.
Figure 1B:
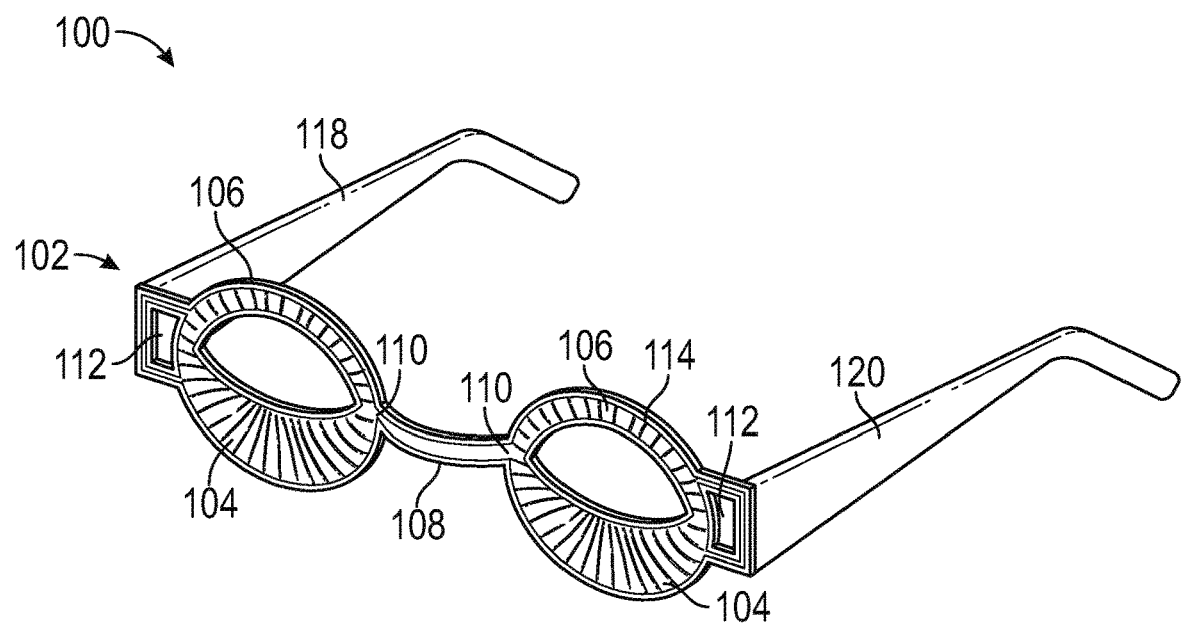
FIG. 1B is a perspective of the device of FIG. 1A not worn by a user.

FIG. 1 illustrates a device 100 comprising a frame 102 and an energy source 104 operably coupled to the frame 102 that can apply energy to eyelids and can allow for normal blinking of the eye. The frame 102 can be securably positionable on a face of a user. The frame 102 can comprise an engagement portion 106 operably coupled to a support portion 108. The engagement portion 106 can be positionable over an eye of a user. The engagement portion 106 can extend between a medial side and a lateral side thereof. The support portion 108 can be securable to the face of the user peripheral to an eye area thereof. The eye area can comprise both the upper eyelid and the lower eyelid of the eye. The engagement portion 106 of the frame 102 can either be suspended in front of or positionable in contact with the upper eyelid or the lower eyelid when the frame 102 is positioned on the face of the user. In some examples, the frame 102 can urge the engagement portion 106 into contact with the upper eyelid or the lower eyelid of at least one of the eyes of the user. The engagement portion 106 can be contoured to match the shape of the upper eyelid or the lower eyelid of the eye of the user. The engagement portion 106 can be further contoured to follow the location of the Meibomian glands when the frame 102 is positioned on the face of the user. Additionally or alternatively, the engagement portion 106 can be moldable to match the curvature of the upper eyelid or the lower eyelid or to follow the location of the Meibomian glands. At least a portion of the frame 102 can define a lumen 114 for at least partially containing the energy source 104 therein.

The engagement portion 106 can comprise a first engagement portion 106 and the frame 102 can further comprise a second engagement portion 106 spaced apart from the first engagement portion 106. The first engagement portion 106 and the second engagement portion 106 can be coupled via a support portion 108 extending therebetween. In one example, the support portion 108 can be positionable on a portion of the nose of the user. The support portion 108 can further comprise a first earpiece 118 and a second earpiece 120. Each of the first and second earpiece 120 can be engageable with a respective ear of the user. The first earpiece 118 can be coupled to and extend away from the lateral side of the first engagement portion 106, and the second earpiece 120 can be coupled to and extend away from the lateral side of the second engagement portion 106.

The energy source 104 can be removably coupleable to the frame 102. Additionally or alternatively, the energy source 104 can comprise an exothermic energy source or an endothermic energy source. In one example, the energy source 104 can comprise sodium acetate, such as super saturated sodium acetate and the like. In a further example, the energy source 104 can further comprise a stainless steel trigger to activate the super saturated sodium acetate to form a re-usable energy source 104. The sodium acetate/stainless steel trigger can be activated upon agitation then can be heated (e.g., boiled) to reverse the reaction, readying the energy source 104 for the subsequent use. Additionally or alternatively, the energy source 104 can comprise a gel.

Figure 2:
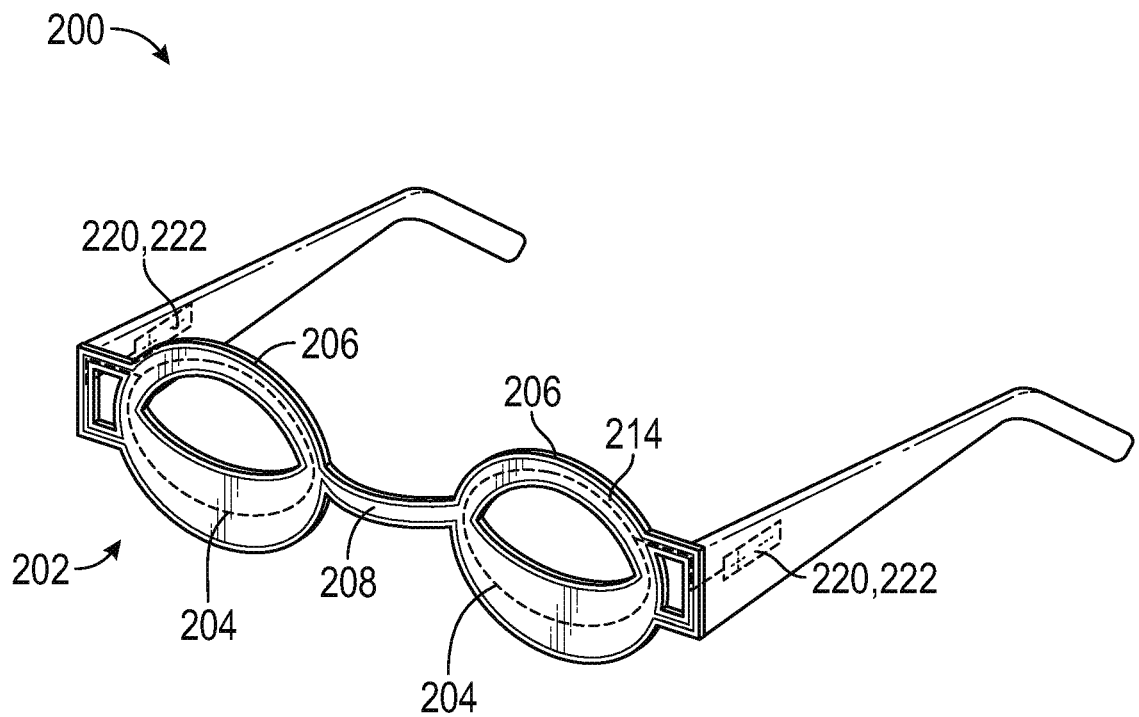
FIG. 2 is a perspective view of another example of a device according to the present disclosure.

In another example illustrated in FIG. 2, the device 200 can comprise a frame 202 including engagement portions 206 and a support portion 208. The device 200 can include an energy source 204 that can comprise a thermal energy source or a vibrational energy source. In an example, the energy source 204 can comprise a conductor 218. The energy source 204 can further comprise a power source 220, such as a battery or the like, or a controller 222 for regulating the energy source. The controller 222 can comprise a timer or a temperature controller. Additionally or alternatively, the energy source can further comprise an insulator. The conductor 218 can be embedded in the insulator. In some aspects, at least a portion of the frame 202 can comprise the insulator.

The frame can optionally comprise a stem that can extend from the engagement portion towards the eye of the user. The stem can promote blinking of the eye when the frame is positioned on the face of the user.

Figure 3:
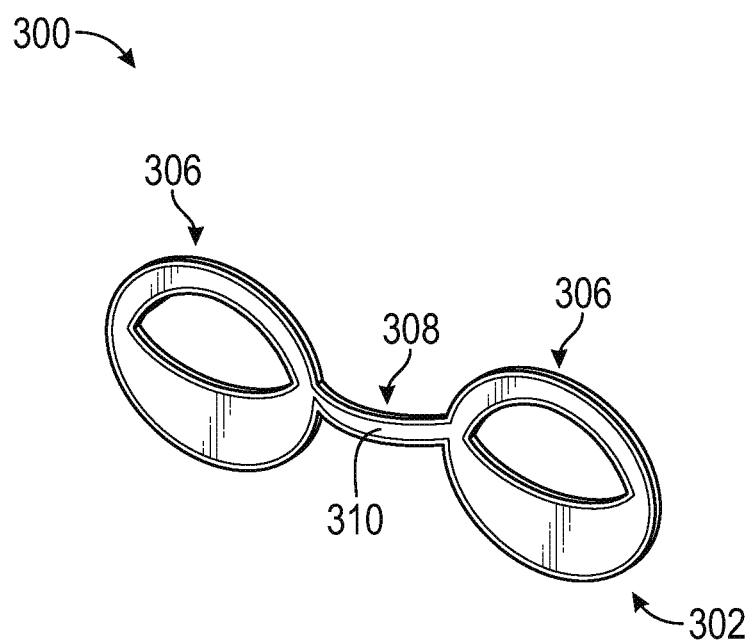
FIG. 3 is a perspective view of another example of a device according to the present disclosure.

In another example illustrated in FIG. 3, the device 300 can comprise a frame 302 including engagement portions 306 and a support portion 308. The support portion 308 can comprise a resilient member 310 that can apply pressure to opposing sides of the bridge of the nose of a user when the device 300 is positioned on the face of the user.

Figure 4:
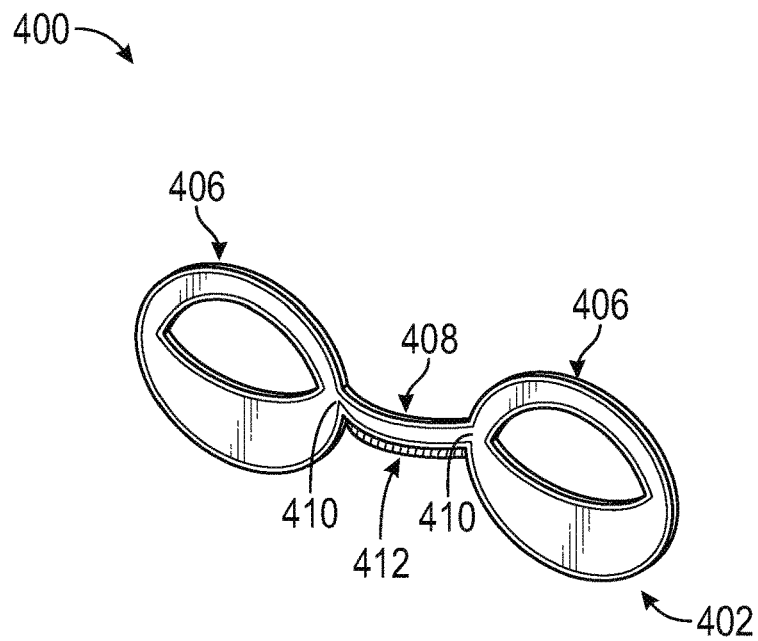
FIG. 4 is a perspective view of another example of a device according to the present disclosure.

In another example illustrated in FIG. 4, the device 400 can comprise a frame 402 including engagement portions 406 and a support portion 408. The support portion 408 can comprise an adhesive 412 for adhering the support portion 408 to a portion of the nose of the user when the device is positioned on the face of a user. Application of the adhesive 412 outside of the eye area (i.e., the upper and lower eyelid) but proximate to the eyelid promotes the intended engagement between the engagement portion(s) 306 and at least one of the upper and lower eyelids of an eye while avoiding the sensitive eyelid skin as well as any inhibition of natural blinking of the eye.

Figure 5:
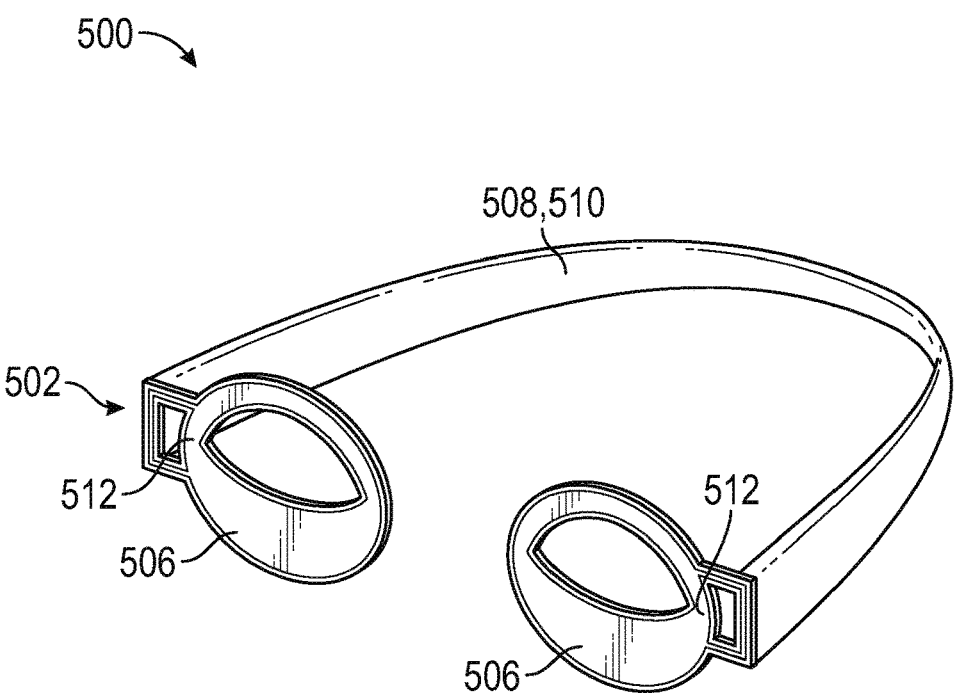
FIG. 5 is a perspective view of another example of a device according to the present disclosure.

In another example illustrated in FIG. 5, the device 500 can comprise a frame 502 including engagement portions 506 and a support portion 508. The support portion 508 comprises a resilient member 510 that can extend between a lateral side 512 of the first engagement portion and a lateral side 512 of the second engagement portion. The resilient member 510 is positionable around an occipital portion of a head of the user. The resilient member 510 can be configured to urge the first engagement portion 506 and the second engagement portion 506 to each contact the upper lid or the lower lid of a respective eye of the user at a substantially uniform pressure when positioned around the occipital portion of the head of the user.

In any of the examples discussed herein, the frame can comprise a polymer such as, but not limited to, vinyl and the like.

Figure 6:
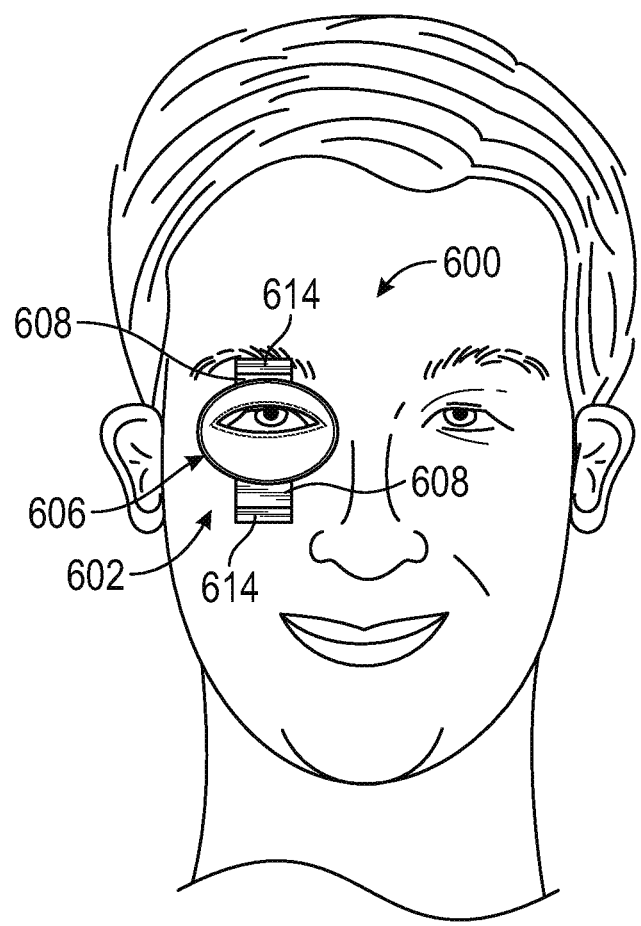
FIG. 6 is a perspective view of another example of a device according to the present disclosure.

In another example illustrated in FIG. 6, the device 600 can comprise a frame 602 including an engagement portion 606 and a support portion 608. A first end of the support portion 608 can be coupled to the engagement portion 606 and a second end of the support member opposite the first end can extend away from the engagement portion 606. A region proximate the second end can comprise an adhesive portion 614. The adhesive portion 614 of the support member 608 can be adherable to at least one location on a user. The at least one location can be a region superior to the eye area, a region inferior to the eye area, a temporal region, or a nasal region. The eye area can include the upper eyelid and the lower eyelid of a respective eye. As with the example of FIG. 4, application of the adhesive portions 614 outside of the eye area but proximate to the eyelid promotes the intended engagement between the engagement portion 606 and at least one of the upper and lower eyelids of an eye while avoiding the sensitive eyelid skin as well as any inhibition of natural blinking of the eye.

The present subject matter also provides for a method for treating an eye. The method can comprise: (i) securably positioning a frame of a device to a face of a user, the device comprising: a frame that can be securably positionable on a face of a user, the frame comprising an engagement portion that can be operably coupled to a support portion, wherein the engagement portion can be positionable over an eye of a user, wherein the engagement portion can extend between a medial side and a lateral side, wherein at least a portion of the engagement portion can be contoured to match the shape of an upper eyelid or a lower eyelid of the eye of the user, wherein the support portion can be securable to the face of the user peripheral to an eye area thereof; and an energy source operably coupled to the frame; wherein the frame and the energy source cooperate to apply energy to the upper eyelid or the lower eyelid of the eye of the user without obstructing use of or normal blinking of the eye; and (ii) activating the energy source to apply energy to the upper eyelid or the lower eyelid of the eye of the user for a selected time and at a selected temperature. Securably positioning the frame of the device to the face of a user can comprise suspending the engagement portion proximate the upper eyelid or the lower eyelid or contacting the upper eyelid or the lower eyelid with the engagement portion. Contacting the upper eyelid or the lower eyelid with the engagement portion can further comprise applying pressure to the upper eyelid or the lower eyelid.

The selected time can be from about 10 minutes to about 30 minutes. The selected temperature can be from about 20 degrees to about 55 degrees Celsius, more particularly, from about 38 degrees to about 48 degrees Celsius, and, most particularly, from about 40 degrees to about 44 degrees Celsius.

The method can optionally comprise applying a pharmaceutical agent, a biological agent, or a chemical agent to at least a portion of the eye area of the user.

VARIOUS NOTES AND EXAMPLES

Example 1 is a device, comprising: a frame securably positionable on a face of a user, the frame comprising an engagement portion operably coupled to a support portion, the engagement portion positionable over an eye of a user, the engagement portion extending between a medial side and a lateral side thereof, wherein the support portion is securable to the face of the user peripheral to an eye area thereof, wherein the eye area comprises both the upper eyelid and the lower eyelid of the eye; and an energy source operably coupled to the frame; wherein at least a portion of the engagement portion is configured to provide energy to an upper eyelid or a lower eyelid of the eye of the user, wherein the frame and the energy source cooperate to apply energy to the upper eyelid or the lower eyelid of the eye of the user without obstructing use or normal blinking of the eye.

In Example 2, the subject matter of Example 1 optionally includes wherein the engagement portion comprises a first engagement portion, wherein the frame further comprises a second engagement portion spaced apart from the first engagement portion.

In Example 3, the subject matter of Example 2 optionally includes wherein the first engagement portion and the second engagement portion are coupled via the support portion, the support portion extending between the respective medial sides of the first engagement portion and the second engagement portion, wherein the support portion is positionable on a portion of a nose of the user.

In Example 4, the subject matter of Example 3 optionally includes wherein the support portion comprises a resilient member that applies pressure to opposing sides of the bridge of the nose of the user.

In Example 5, the subject matter of anyone or more of Examples 3-4 optionally include wherein the support portion comprises an adhesive for adhering the support portion to a portion of the nose of the user.

In Example 6, the subject matter of anyone or more of Examples 3-5 optionally include wherein the support portion further comprises a first earpiece and a second earpiece, each of the first and second earpiece being engageable with a respective ear of the user, the first earpiece coupled to and extending away from the lateral side of the first engagement portion, and the second earpiece coupled to and extending away from the lateral side of the second engagement portion.

In Example 7, the subject matter of anyone or more of Examples 2-6 optionally include wherein the support portion comprises a resilient member extending between a lateral side of the first engagement portion and a lateral side of the second engagement portion, the resilient member being positionable around an occipital portion of a head of the user.

In Example 8, the subject matter of Example 7 optionally includes wherein the resilient member urges the first engagement portion and the second engagement portion to each contact the upper lid or the lower lid of a respective eye of the user at a substantially uniform pressure when positioned around the occipital portion of the head of the user.

In Example 9, the subject matter of anyone or more of Examples 1-8 optionally include wherein a first end of the support portion is coupled to the engagement portion and a second end of the support member opposite the first end extends away from the engagement portion, wherein a region proximate the second end comprises an adhesive.

In Example 10, the subject matter of Example 9 optionally includes wherein the adhesive portion of the anchor is adherable to at least one location, wherein the at least one location is a region superior to the eye area, a region inferior to the eye area, a temporal region, or a nasal region.

In Example 11, the subject matter of anyone or more of Examples 1-10 optionally include wherein the engagement portion is positionable in contact with the upper eyelid or the lower eyelid when the frame is positioned on the face of the user.

In Example 12, the subject matter of Example 11 optionally includes wherein the frame urges the engagement portion into contact with the upper eyelid or the lower eyelid of the at least one eye of the user.

In Example 13, the subject matter of anyone or more of Examples 1-12 optionally include wherein the engagement portion is further contoured to follow the location of the Meibomian glands when the frame is positioned on the face of the user.

In Example 14, the subject matter of anyone or more of Examples 1-13 optionally include wherein at least the engagement portion of the frame is moldable to match the curvature of the upper eyelid or the lower eyelid.

In Example 15, the subject matter of anyone or more of Examples 1-14 optionally include wherein the energy source comprises an exothermic energy source or an endothermic energy source.

In Example 16, the subject matter of Example 15 optionally includes wherein the energy source is an exothermic energy source comprising sodium acetate.

In Example 17, the subject matter of anyone or more of Examples 1-16 optionally include wherein the energy source comprises a thermal energy source or a vibrational energy source.

In Example 18, the subject matter of anyone or more of Examples 1-17 optionally include wherein the energy source comprises a conductor.

In Example 19, the subject matter of Example 18 optionally includes wherein the energy source further comprises an insulator and wherein the conductor is embedded in the insulator.

In Example 20, the subject matter of anyone or more of Examples 18-19 optionally include wherein the energy source further comprises a battery.

In Example 21, the subject matter of anyone or more of Examples 1-20 optionally include wherein the frame defines a lumen for at least partially containing the energy source therein.

In Example 22, the subject matter of anyone or more of Examples 1-21 optionally include wherein the energy source is removably coupleable to the frame.

In Example 23, the subject matter of Example 22 optionally includes wherein the energy source comprises a gel.

In Example 24, the subject matter of anyone or more of Examples 1-23 optionally include wherein the energy source further comprises a controller for regulating the energy source.

In Example 25, the subject matter of Example 24 optionally includes wherein the controller comprises a timer or a temperature controller.

In Example 26, the subject matter of anyone or more of Examples 1-25 optionally include wherein device further comprises a stem extending from the engagement portion towards the eye for promoting blinking thereof when the frame is positioned on the face of the user.

In Example 27, the subject matter of anyone or more of Examples 1-26 optionally include wherein at least a portion of the engagement portion is contoured to match the shape of the upper eyelid or the lower eyelid of the eye of the user.

Example 28 is a method, comprising: securably positioning a frame of a device to a face of a user, the device comprising: a frame securably positionable on a face of a user, the frame comprising an engagement portion operably coupled to a support portion, the engagement portion positionable over an eye of a user, the engagement portion extending between a medial side and a lateral side thereof, at least a portion of the engagement portion being contoured to match the shape of an upper eyelid or a lower eyelid of the eye of the user, wherein the support portion is securable to the face of the user peripheral to an eye area thereof; and an energy source operably coupled to the frame; wherein the frame and the energy source cooperate to apply energy to the upper eyelid or the lower eyelid of the eye of the user without obstructing use of or normal blinking of the eye; and activating the energy source to apply energy to the upper eyelid or the lower eyelid of the eye of the user for a time of from about 10 minutes to about 30 minutes and at a temperature of from about 20 degrees to about 55 degrees Celsius.

In Example 29, the subject matter of Example 28 optionally includes wherein the temperature is from about 38 degrees to about 48 degrees Celsius.

In Example 30, the subject matter of Example 29 optionally includes wherein the temperature is from about 40 degrees to about 44 degrees Celsius.

In Example 31, the subject matter of anyone or more of Examples 28-30 optionally include applying a pharmaceutical agent, a biological agent, or a chemical agent to at least a portion of the eye area of the user.

In Example 32, the subject matter of anyone or more of Examples 28-31 optionally include wherein securably positioning the frame of the device to the face of the user further comprises suspending the engagement portion proximate the upper eyelid or the lower eyelid.

In Example 33, the subject matter of anyone or more of Examples 28-32 optionally include wherein securably positioning the frame of the device to the face of the user further comprises contacting the upper eyelid or the lower eyelid with the engagement portion.

In Example 34, the subject matter of Example 33 optionally includes wherein contacting the upper eyelid or the lower eyelid with the engagement portion further comprises applying pressure thereto.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A device, comprising:
    a frame securably positionable on a face of a user, the frame comprising:
    an engagement portion positionable over an eye of the user, the engagement portion extending between a medial side and a lateral side thereof, wherein the engagement portion comprises a first engagement portion and a second engagement portion spaced apart from the first engagement portion;

a support portion is securable to the face of the user peripheral to an eye area thereof the eye area comprising both an upper eyelid and a lower eyelid of the eye, the support portion is positionable on a portion of a nose of the user, the support portion comprising a resilient member that applies pressure to opposing sides of a bridge of the nose of the user, wherein the engagement portion is operably coupled to the support portion, and the first engagement portion and the second engagement portion are coupled to each other via the support portion, the support potion extending between the respective medial sides of the first engagement portion and the second engagement portion; and a reusable energy source situated on the engagement portion of the frame, the reusable energy source comprising supersaturated sodium acetate and a metallic trigger, the reusable energy source being an exothermic energy source that can be activated upon agitation, wherein the reusable energy source is operable to apply energy to the upper eyelid or the lower eyelid of the eye of the user via at least a portion of the engagement portion without obstructing use or normal blinking of the eye.

2. The device of claim 1, wherein the support portion comprises an adhesive for adhering the support portion to a portion of the nose of the user.

3. The device of claim 1, wherein the support portion further comprises a first earpiece and a second earpiece, each of the first and second earpiece being engageable with a respective ear of the user, the first earpiece coupled to and extending away from the lateral side of the first engagement portion, and the second earpiece coupled to and extending away from the lateral side of the second engagement portion.

4. The device of claim 1, wherein the support portion comprises a resilient member extending between a lateral side of the first engagement portion and a lateral side of the second engagement portion, the resilient member being positionable around an occipital portion of a head of the user.

5. The device of claim 4, wherein the resilient member urges the first engagement portion and the second engagement portion to each contact the upper lid or the lower lid of a respective eye of the user at a substantially uniform pressure when positioned around the occipital portion of the head of the user.

6. The device of claim 1, wherein a first end of the support portion is coupled to the engagement portion and a second end of the support member opposite the first end extends away from the engagement portion, wherein a region proximate the second end comprises an adhesive.

7. The device of claim 6, wherein the adhesive is adherable to at least one location, wherein the at least one location is a region superior to the eye area, a region inferior to the eye area, a temporal region, or a nasal region.

8. The device of claim 1, wherein the engagement portion is positionable in contact with the upper eyelid or the lower eyelid when the frame is positioned on the face of the user.

9. The device of claim 8, wherein the frame urges the engagement portion into contact with the upper eyelid or the lower eyelid of the at least one eye of the user.

10. The device of claim 1, wherein the engagement portion is further contoured to follow the location of the Meibomian glands when the frame is positioned on the face of the user.

11. The device of claim 1, wherein at least the engagement portion of the frame is moldable to match the curvature of the upper eyelid or the lower eyelid.

12. The device of claim 1, wherein the reusable energy source comprises a thermal energy source or a vibrational energy source.

13. The device of claim 1, wherein at least a portion of the engagement portion is contoured to match shape of the upper eyelid or the lower eyelid of the eye of the user.

* * * * *